United States Patent [19]

Harada

[11] Patent Number: 4,928,700
[45] Date of Patent: May 29, 1990

[54] PULSE WAVE DETECTING APPARATUS

[75] Inventor: Chikao Harada, Nagoya, Japan

[73] Assignee: Colin Electronics Co., Ltd., Aichi, Japan

[21] Appl. No.: 299,410

[22] Filed: Jan. 23, 1989

[30] Foreign Application Priority Data

Jan. 28, 1988 [JP] Japan .............................. 63-10112[U]

[51] Int. Cl.$^5$ .............................................. A61B 5/02
[52] U.S. Cl. .................................... 128/672; 128/687
[58] Field of Search ......................... 128/672, 677–690; 340/653, 660, 663, 309.15, 309.2

[56] References Cited

U.S. PATENT DOCUMENTS

| | | | |
|---|---|---|---|
| 3,737,887 | 6/1973 | Wakamatsu et al. | 340/653 |
| 3,811,429 | 5/1974 | Fletcher et al. | |
| 3,992,668 | 11/1976 | Finger | 340/653 X |
| 4,106,002 | 8/1978 | Hogue, Jr. | |
| 4,117,526 | 9/1978 | Bates | 340/663 X |
| 4,799,491 | 1/1989 | Eckerle | 128/672 |

FOREIGN PATENT DOCUMENTS 0170484 2/1986 European Pat. Off. .

OTHER PUBLICATIONS

Mesures Regulation Automatisme, vol. 44, No. 5, May 1979, pp. 73–74, Paris, FR; "Techniques d'Applications", p. 74, (w/translation).

Primary Examiner—Angela D. Sykes
Attorney, Agent, or Firm—Oliff & Berridge

[57] ABSTRACT

A pulse wave detecting apparatus having a pressure-sensitive semiconductor element for detecting pulsation of an artery of a subject and converting the detected pulsation into electrical signal, the electrical signal representing pulse wave corresponding to the pulsation, the semiconductor element being pressed against a body surface of the subject such that the semiconductor element is aligned with the artery via the body surface, the apparatus including a timer device for measuring operation time of the pressure-sensitive semiconductor element, and generating a full-use signal when the measured operation time exceeds a reference value representing that the semiconductor element has been fully operated up to its permitted operation time.

6 Claims, 2 Drawing Sheets

PULSE WAVE DETECTING APPARATUS

BACKGROUND OF THE INVENTION

1. Field of the Invention

The present invention relates to a pulse wave detecting apparatus for detecting pulse wave produced by an arterial vessel of a living body.

2. Related Art Statement

The Applicant and others filed Japanese Patent Application No. 62-130879 in which they disclosed a pulse wave detecting apparatus having a semiconductor element which is pressed against a body surface of a subject such that the element is aligned with an arterial vessel of the subject, for detecting pulsation of the arterial vessel and converting the detected pulsation into electrical signal representing pulse wave corresponding to the pulsation. The above-indicated Japanese Patent Application was laid open under Publication No. 63-293424 on Nov. 30, 1988, which date is subsequent to the priority date Jan. 28, 1988 for the present application.

The properties of the above semiconductor element, however, usually change as time elapses. The semiconductor element whose properties have changed considerably largely after use over a long period of time, is inappropriate to further use for the pulse wave detecting apparatus, because pulse wave cannot be detected with sufficient accuracy through such semiconductor element.

SUMMARY OF THE INVENTION

It is therefore an object of the present invention to provide a pulse wave detecting apparatus which is capable of preventing the semiconductor element thereof from being operated beyond a permitted operation time.

The above object has been achieved by the present invention, which provides a pulse wave detecting apparatus having a pressure-sensitive semiconductor element for detecting pulsation of an artery of a subject and converting the detected pulsation into electrical signal, the electrical signal representing pulse wave corresponding to the pulsation, the semiconductor element being pressed against a body surface of the subject such that the semiconductor element is aligned with the artery via the body surface, the apparatus comprising timer means for measuring operation time of the pressure-sensitive semiconductor element, and generating a full-use signal when the measured operation time exceeds a reference value representing that the semiconductor element has been fully used.

In the pulse wave detecting apparatus constructed as described above, the timer means detects operation time of the semiconductor element and generates a full-use signal when the detected operation time exceeds a permitted operation time. By utilizing the full-use signal, the pulse wave detecting apparatus can inhibit the semiconductor element from being used beyond the permitted operation time, thereby preventing deteriorated accuracy of detection of pulse wave due to the changed properties of the semiconductor element.

According to a preferred embodiment of the present invention, the pulse wave detecting apparatus further comprises (a) a semiconductor chip, and (b) control means, the pressure-sensitive semiconductor element being formed on the semiconductor chip, the pulse-wave electrical signal from the semiconductor element being supplied to the control means, the control means monitoring blood pressure of the subject based on the pulse-wave electrical signal from the semiconductor element.

According to another embodiment of the present invention, the pulse wave detecting apparatus further comprises a housing for accommodating the pressure-sensitive semiconductor element, the timer means being secured to the housing.

In yet another embodiment of the pulse wave detecting apparatus of the invention, the timer means comprises (a) a glass tube, (b) a pair of electrodes held in the glass tube such that the pair of electrodes are spaced apart from each other in the glass tube, (c) electrolytic solution held in the glass tube such that the electrolytic solution fills a space defined by the glass tube and the pair of electrodes, and (d) a photoelectric switch for detecting the space, direct current being applied between the pair of electrodes while the pressure-sensitive semiconductor element is operated, whereby the space is moved in the glass tube relative thereto, the photoelectric switch generating the full-use signal when detecting that the space has been moved to a predetermined position in the glass tube.

In a further embodiment of the pulse wave detecting apparatus of the invention, the timer means comprises (a) a discharge circuit including a battery and a resistance connected in series to the battery, and (b) a comparator circuit for comparing a voltage of the battery with a reference voltage, the battery discharging while the semiconductor element is operated, the comparator circuit generating the full-use signal when detecting that the voltage of the battery has fallen below the reference voltage.

BRIEF DESCRIPTION OF THE DRAWINGS

The above and optional objects, features and advantages of the present invention will be better understood by reading the following detailed description of the presently preferred embodiment of the invention, when considered in conjunction with the accompanying drawings, in which.

DETAILED DESCRIPTION OF THE PREFERRED EMBODIMENT

Figure 1:
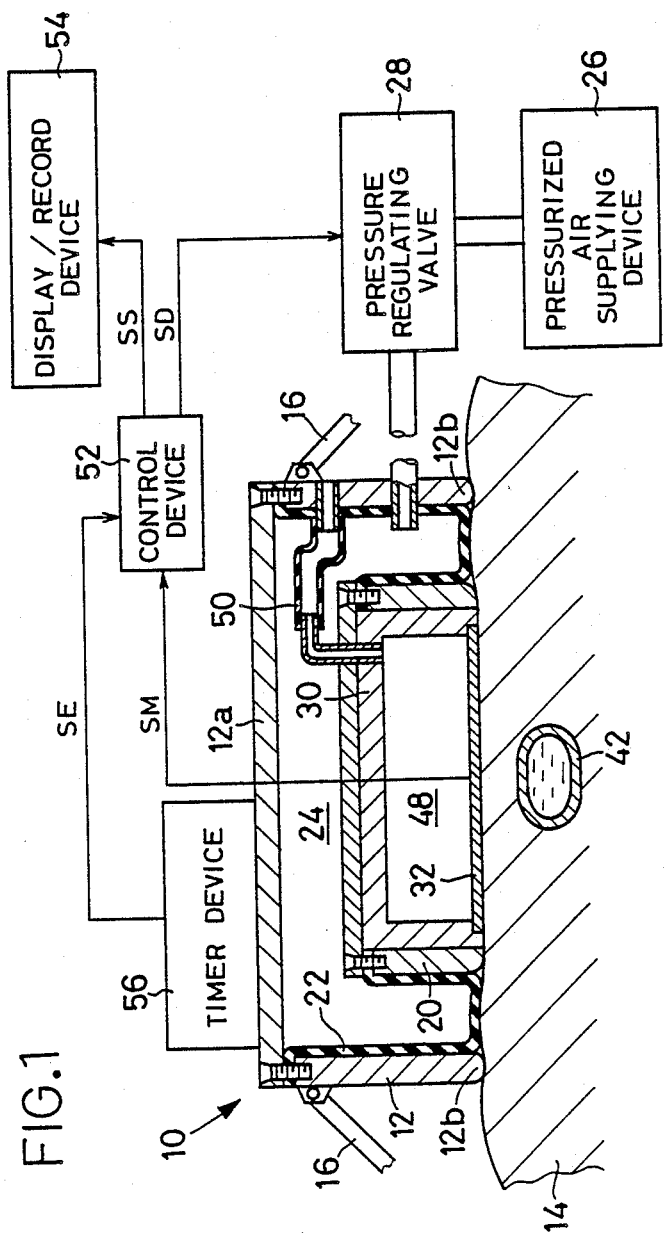
FIG. 1 is an illustrative view showing an electrical circuit of a pulse wave detecting apparatus of the present invention which has a pulse wave sensor.

Referring first to FIG. 1, there is shown a pulse wave detecting apparatus embodying the present invention. In the figure, reference numeral 10 designates a pulse wave sensor. The pulse wave sensor 10 has a cylindrical housing 12 with a bottom wall 12a. The sensor housing 12 is detachably secured to a surface of a wrist 14 of a subject with the help of a band 16, with a circular open end 12b thereof facing the wrist surface 14. The pulse wave sensor 10 is connected to a control device 52 (described below), when pulse wave is detected. A cylindrical presser member 20 with a bottom wall is accommodated in the housing 12. The presser member 20 is secured to the housing 12 through a diaphragm 22 such that the presser member 20 is movable toward the wrist surface 14 relative to the housing 12, and such that an air-tight space 24 is defined by the presser member 20, housing 12 and diaphragm 22. The air-tight space 24 is supplied with pressurized air from a pressurized-air supplying device 26 via a pressure-regulating valve 28.

Figure 2:
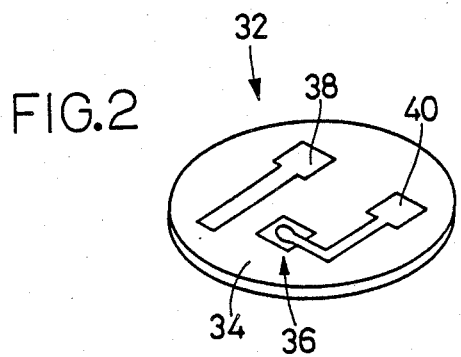
FIG. 2 is a perspective view of a presser plate of the pulse wave sensor of FIG. 1.

A circular presser plate 32 is secured to a circular open end of the presser member 20 via a holding member 30 which is made of electrically insulating material. As shown in FIG. 2, the presser plate 32 consists of a semiconductor chip 34 formed of monocrystalline silicon or the like, and a pressure-sensitive diode 36 formed on a surface of the semiconductor chip 34. Electrical signal which is produced between a pair of terminals 38, 40, represents pressure variation at an interface between the chip 34 and the diode 36. This electrical signal is utilized as pulse wave signal SM representing pulse wave which corresponds to pulsation of a radial artery 42 (FIG. 1). In the present embodiment, the pressure-sensitive diode 36 corresponds to the pressure-sensitive semiconductor element for the pulse wave detecting apparatus. A vacant space 48 defined by the presser member 20 (holding member 30) and the presser plate 32 communicates with ambient air outside the housing 12 via a rubber tube 50 and other members. Thus, the space 48 is free from pressure variation due to body temperature of the subject, for example.

The pulse wave signal SM from the pressure-sensitive diode 36 is applied to the control device 52. The control device 52 has a microcomputer, and generates drive signal SD to the pressure-regulating valve 28 for adjusting pressure level of the pressurized air supplied to the air-tight space 24. The control device 52 processes the pulse wave signal SM from the pressure-sensitive diode 36 and generates display signal SS to a display/record device 54, which device displays and records the pulse wave of the artery 42 in response to the signal SS received.

Figures 3, 4:
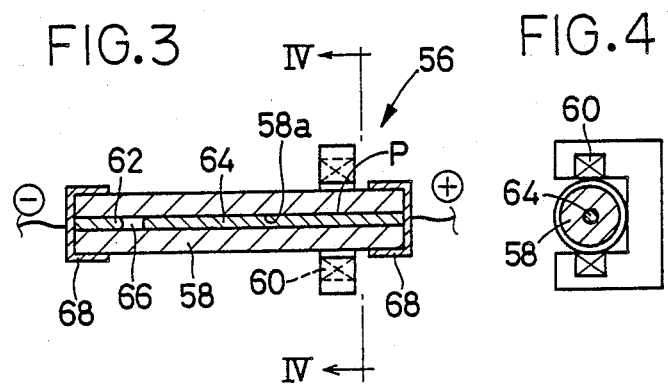
FIG. 3 is a cross-sectional view of a part of a timer device of the apparatus of FIG. 1.
FIG. 4 is a cross-sectional view of the timer device, taken along the line IV—IV of FIG. 3.

A timer device 56 is fixed to an outer surface of the bottom wall 12a of the housing 12 of the pulse wave sensor 10. As shown in FIGS. 3 and 4, the timer device 56 includes a cylindrical glass tube 58 with a through hole 58a extending along a longitudinal axis of the glass tube 58, and a photoelectric switch 60 with a pair of arms between which the glass tube 58 extends through. A pair of electrodes 62, 64 of copper, for example, are inserted into the through hole 58a of the glass tube 58 from opposite ends thereof, respectively. A space 66 defined by the glass tube 58 and the pair of electrodes 62, 64 is filled with suitable electrolyte solution, such as water solution of copper sulfate, together with depolarizer. The opposite ends of the glass tube 58 are sealed by a pair of metallic caps 68, respectively, such that the pair of caps 68 contact the corresponding electrodes 62, 64. At the time the pulse wave sensor 10 is connected to the control device 52, the control device 52 is operated to apply a constant, small current between the pair of electrodes 62, 64 via the pair of metallic caps 68. While the sensor 10 is in connection to the control device 52, namely, while the pressure-sensitive diode 36 is operated, electrolysis is progressed together with shortening (dissolving) of one of the electrodes 64 and lengthening (depositing) of the other electrode 62, whereby the space 66 is moved rightward as viewed in FIG. 3. In the present embodiment, when the operation time of the pressure-sensitive diode 36 reaches a reference value corresponding to a permitted operation time for the diode 36, namely, representing that the diode 36 has been fully used up to the permitted operation time, the space 66 is moved to a position indicated at P in the glass tube 58 which position is aligned with the photoelectric switch 60. When the space 66 is aligned with the photoelectric switch 60, the switch 60 is operated to generate a full-use signal SE to the control device 52. In other words, related parameters such as the magnitude of the constant current applied to the pair of electrodes 62, 64 while the diode 36 is operated, and the initial relative position relationship between the photoelectric switch 60 and the electrolyte solution-holding space 66, are so predetermined that, if the operation time of the pressure-sensitive diode 36 exceeds its permitted operation time (reference value), the switch 60 is operated to generate the full-use signal SE. When receiving the full-use signal SE, the control device 52 operates the display/record device 54 to display an indication that the pressure-sensitive diode 36 has been fully operated up to its permitted operation time. It is recommended that an outer surface of the glass tube 58 be provided with a scale, so that an operator can see how long the diode 36 has been used, from a currently observed relative position of the space 66 with respect to the scale.

As is apparent from the foregoing, in the present embodiment, the timer device 56 measures an operation time of the pressure-sensitive diode 36 and generates a full-use signal SE when the measured operation time exceeds a permitted operation time predetermined for the diode 36, and the display/record device 54 indicates that the diode 36 has been fully used up to the permitted operation time, in response to the signal SE received. Thus, the instant pulse wave detecting apparatus prevents the pulse-wave sensor 10 whose pressure-sensitive diode 36 has been fully used up to its permitted operation time, from further being used. Consequently, the detecting apparatus is free from the problem that pulse wave is detected with deteriorated accuracy due to the changed properties of the diode 36.

While in the illustrated embodiment the photoelectric switch 60 is of a transmission type, it is possible to use a reflection-type photoelectric switch.

Although in the illustrated embodiment the display/record device 54 displays, based on the full-use signal SE, an indication that the pressure-sensitive diode 36 has been fully operated up to its permitted operation time, it is possible to adapt the control device 52 to cease monitoring blood pressure of the subject based on the pulse-wave signal SM from the sensor 10 (diode 36) when receiving the full-use signal SE, in addition to, or in place of, the above-indicated 'full-use' indication by the display/record device 54, in the case where the control device 52 is adapted to monitor the blood pressure of the subject based on the detected pulse wave signal SM.

Figure 5:
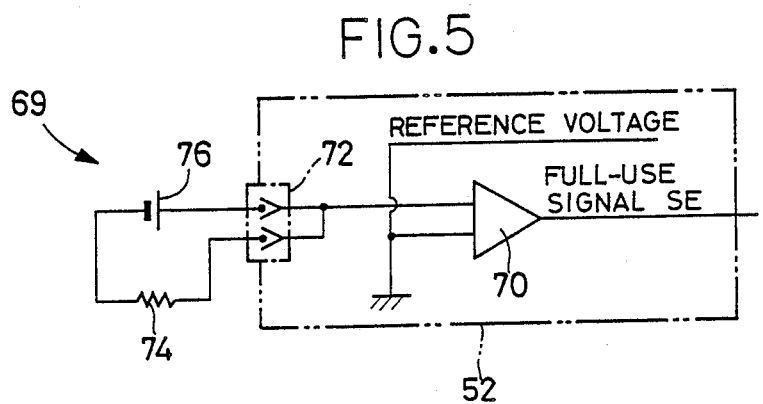
FIG. 5 is a view showing an electrical circuit of another timer device.

Referring to FIG. 5, there is shown another timer device for the pulse wave detecting apparatus. In the figure, the control device 52 includes a comparator 70 having a pair of input terminals one of which always is supplied with a reference voltage and the other of which is coupled to a pair of terminals of a connector 72 disposed with the control device 52. A battery 76 and a resistance 74 connected in series to the battery 76, are disposed with the pulse wave sensor 10. When pulse wave is detected, the sensor 10 is connected to the control device 52, namely, the positive and negative terminals of the battery 76 and resistance 74 are connected to the pair of terminals of the connector 72 of the control device 52, respectively. With the sensor 10 connected to the control device 52, the battery 72 discharges and applies an electrical voltage to the above-indicated other terminal of the comparator 70. The comparator 70 compares the voltage applied by the battery 76 with the reference voltage present at the above-mentioned one input terminal thereof, and generates a full-use signal SE indicating that the pressure-sensitive diode has been fully used up to its permitted operation time, when the applied voltage has fallen below the reference voltage. Related parameters such as the rated output voltage of the battery 70 and the resistance value of the resistance 74 are so predetermined that the time required for the voltage of the battery 76 to be decreased down to the reference voltage, substantially coincides with the permitted operation time of the diode 36. In place of the battery 76, it is possible to employ an electrically charged capacitance of a large capacity, for example 10,000 μF.

While the illustrated pulse-wave detecting apparatus utilizes a single pressure-sensitive diode 36, the principle of the present invention may be applied to an apparatus of the type wherein a plurality of pressure-sensitive diodes are provided and one of those is selected and utilized to obtain pulse wave of an arterial vessel.

Further, in place of the pressure-sensitive diode used in the illustrated embodiment, it is possible to employ a pressure-sensitive semiconductor element of other sorts such as a pressure-sensitive transistor.

While the present invention has been described with detailed particularities of the preferred embodiment, it is to be understood that the present invention may be embodied with various changes, modifications and improvements which may occur to those skilled in the art without departing from the spirit and scope of the invention defined in the following claims.

What is claimed is:

1. A blood pressure monitoring apparatus comprising:
   a pressure sensitive semiconductor element for detecting pulse wave produced from an arterial vessel of a subject, and generating a pulse wave signal representing the detected pulse wave, the semiconductor element being pressed against said arterial vessel via a body surface of the subject so as to detect the pulse wave;
   a housing for accommodating said semiconductor element;
   control means for monitoring blood pressure of the subject based on the pulse wave signal supplied from said semiconductor element, said housing and said control means being separate from each other, and connectable to each other; and
   timer means for measuring an operation time of said semiconductor element, and generating a full-use signal when said operation time exceeds a reference value which represents that the semiconductor element has been used for a permitted period of time, said timer means being supported by said housing.

2. The apparatus as recited in claim 1, further comprising
   a semiconductor chip,
   said pressure-sensitive semiconductor element being formed on said semiconductor chip.

3. The apparatus as recited in claim 1, wherein said timer means comprises
   a glass tube having an axial through hole,
   a pair of electrodes held in the through hole of said glass tube such that said pair of electrodes are spaced apart from each other in said through hole,
   an electrolytic solution held in the through hole of said glass tube such that said electrolytic solution fills a space defined in said through hole by said glass tube and said pair of electrodes, and
   a photoelectric switch for detecting said space,
   said control means applying a constant direct current between said pair of electrodes while said pressure-sensitive semiconductor element is operated, whereby said space moves in the through hole of said glass tube relative thereto, said photoelectric switch generating said full-use signal when detecting that said space has moved to a predetermined position in the through hole of said glass tube.

4. The apparatus as recited in claim 1, wherein said timer means comprises
   a discharge circuit including a battery and a resistance connected in series to said battery, and
   a comparator circuit for comparing a voltage of said battery with a reference voltage,
   said battery discharging while said pressure-sensitive semiconductor element is operated, said comparator circuit generating said full-use signal when detecting that said voltage of said battery has fallen below said reference voltage.

5. The apparatus as set forth in claim 1, further comprising
   display means for displaying an indication that said semiconductor element has been used for said permitted period of time,
   said control means being responsive to said full-use signal from said timer means to command said display means to display said indication.

6. The apparatus as set forth in claim 1, wherein said control means is responsive to said full-use signal to cease to monitor blood pressure of the subject.

* * * * *